United States Patent
Kishimoto et al.

(10) Patent No.: US 9,909,119 B2
(45) Date of Patent: Mar. 6, 2018

(54) METHOD FOR PRODUCING PURIFIED SOYBEAN OLIGOSACCHARIDE LIQUID

(71) Applicant: TORAY INDUSTRIES, INC., Tokyo (JP)

(72) Inventors: Jumpei Kishimoto, Kamakura (JP); Shigeyuki Funada, Kamakura (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 24 days.

(21) Appl. No.: 15/034,934

(22) PCT Filed: Nov. 6, 2014

(86) PCT No.: PCT/JP2014/079464
§ 371 (c)(1),
(2) Date: May 6, 2016

(87) PCT Pub. No.: WO2015/068769
PCT Pub. Date: May 14, 2015

(65) Prior Publication Data
US 2016/0264957 A1    Sep. 15, 2016

(30) Foreign Application Priority Data

Nov. 7, 2013  (JP) .................... 2013-231454

(51) Int. Cl.
*C12P 19/14* (2006.01)
*C12N 15/10* (2006.01)
*C12P 19/04* (2006.01)

(52) U.S. Cl.
CPC .......... *C12N 15/1017* (2013.01); *C12P 19/04* (2013.01); *C12P 19/14* (2013.01)

(58) Field of Classification Search
CPC ....................................................... C12P 19/14
See application file for complete search history.

(56) References Cited

U.S. PATENT DOCUMENTS

| | | |
|---|---|---|
| 4,902,673 A | 2/1990 | Hayakawa et al. |
| 2001/0034443 A1 | 10/2001 | Furuta et al. |
| 2003/0157239 A1 | 8/2003 | Oliveira et al. |
| 2012/0070871 A1 | 3/2012 | Sawai et al. |
| 2014/0287461 A1 | 9/2014 | Kurihara et al. |

FOREIGN PATENT DOCUMENTS

| | | |
|---|---|---|
| JP | 59-179064 A | 10/1984 |
| JP | 62-155082 A | 7/1987 |

(Continued)

OTHER PUBLICATIONS

International Search Report, issued in PCT/JP2014/079464, dated Feb. 3, 2015.
Kim et al., "Optimization of the extraction and purification of oligosaccharides from defatted soybean meal", International Journal of Food Science and Technology, 2003, vol. 38, pp. 337-342.
Matano et al., "Production of useful substances from food and agricultural waste -production of ethanol-", Japan Society for Bioscience, Biotechnology, and Agrochemistry Taikai Koen Yoshishu, 2009, p. 335, 3P1358B.

(Continued)

*Primary Examiner* — Rosanne Kosson
(74) *Attorney, Agent, or Firm* — Birch, Stewart, Kolasch & Birch, LLP (57) ABSTRACT

A method for producing a purified soybean oligosaccharide liquid according to the present invention is a method for producing a purified soybean oligosaccharide liquid from a soybean and/or a processed soybean product, comprising: the step (1) of mixing the soybean and/or the processed soybean product with a water-containing polar organic solvent that contains a polar organic solvent and water and then removing a generated precipitate to obtain a soybean oligosaccharide liquid that contains the water-containing polar organic solvent; the step (2) of removing the polar organic solvent from the soybean oligosaccharide liquid to obtain a soybean oligosaccharide suspension; the step (3) of mixing the soybean oligosaccharide suspension with cellulase to obtain a cellulase-treated soybean oligosaccharide suspension; and the step (4) of subjecting the cellulase-treated soybean oligosaccharide suspension to solid-liquid separation to obtain a purified soybean oligosaccharide liquid.

10 Claims, 2 Drawing Sheets

(56) References Cited

FOREIGN PATENT DOCUMENTS

| JP | 62-201606 A | 9/1987 |
| JP | 3-287594 A | 12/1991 |
| JP | 4-187695 A | 7/1992 |
| JP | 2001-252092 A | 9/2001 |
| JP | 2005-500073 A | 1/2005 |
| JP | 2009-189291 A | 8/2009 |
| WO | WO 2010/067785 A1 | 6/2010 |
| WO | WO 2010/140602 A1 | 12/2010 |

OTHER PUBLICATIONS

Matsuo, "Solubilization and structural changes in the bean curd refuse by Plant fiber degradation enzyme", Dai 52 Kai The Japanese Society of Nutrition and Food Science Taikai Koen Yoshishu, 1998, pp. 290, L4.
Sreenath et al., "Lactic acid production from agriculture residues", Biotechnology Letters, 2001, vol. 23, No. 3, pp. 179-184.
Ghose, "Measurement of Cellulase Activities," Pure and Applied Chemistry, vol. 59, No. 2, 1987, pp. 257-268.
Qureshi et al., "Soy molasses as fermentation substrate for production of butanol using Clostridium beijerinckii BA101," Journal of Industrial Microbiology & Biotechnology, vol. 26, 2001, pp. 290-295.
Reis et al., "Hydrolysis of Galacto-oligosaccharides in Soy Molasses by a-galactosidases and Invertase from Aspergillus terreus," Brazilian Archives of Biology and Technology, vol. 53, No. 3, May-Jun. 2010, pp. 719-729.

METHOD FOR PRODUCING PURIFIED SOYBEAN OLIGOSACCHARIDE LIQUID

TECHNICAL FIELD

The present invention relates to a method for producing a purified soybean oligosaccharide liquid from a soybean or a soybean extract.

BACKGROUND ART

A soybean oligosaccharide is a general term for oligosaccharides that are contained in a soybean such as sucrose, raffinose, and stachyose; these have an activity of activating useful bacteria in the intestines and therefore the use thereof mainly as a health food product has drawn much attention. Abundant soybean oligosaccharides are contained also in waste materials such as soybean whey and soybean molasses that are generated in large amounts in an industrial soybean processing step; the waste material such as soybean whey or soybean molasses is therefore expected to be utilized as inexpensive sugar raw materials as well.

As a method for producing monosaccharides or alcohol using the soybean oligosaccharide that is contained in waste materials such as soybean whey or soybean molasses, what has been disclosed are, for example, a method of allowing galactosidase to act on soybean oligosaccharides to obtain monosaccharides (see Non-patent Document 1) and a method comprising subjecting soybean molasses directly to fermentation to produce ethanol or butanol (see Non-patent Document 2).

Further, a method using soybean whey or a defatted soybean as a raw material has been known as a conventional production method for soybean oligosaccharide. Soybean whey is a waste liquid that remains behind after soybeans are subjected to steam cooking to yield broth, that is, soy milk and then proteins are precipitated and removed therefrom by addition of an acid or the like, and is known to contain soybean oligosaccharides, lipids, soluble proteins and the like. As a production method for soybean oligosaccharides using soybean whey as a raw material, what has been disclosed are, for example, a method comprising adding calcium hydroxide to soybean whey, heating the mixture, and precipitating and removing impurities to obtain oligosaccharides (see Patent Document 1) and a method comprising heating soybean whey, adding phosphoric acid thereto to lower the pH, and precipitating and removing impurities to obtain oligosaccharides (see Patent Document 2).

Further, defatted soybeans are a residue obtained by removing lipids from soybeans using a solvent such as hexane. As a method for producing soybean oligosaccharides using the defatted soybean as a raw material, what has been disclosed are for example a method comprising extracting a concentrate that contains *Bifidobacterium*-proliferating substances from defatted soybeans using an aqueous solution of alcohols to obtain oligosaccharides (see Patent Document 3) and a method comprising extracting oligosaccharides by adding water to defatted soybeans and obtaining soybean oligosaccharides from an extract liquid (see Patent Document 4).

PRIOR ART REFERENCES

Patent Documents

Patent Document 1: Japanese Patent Application Laid-Open Publication No. 59-179064
Patent Document 2: Japanese Patent Application Laid-Open Publication No. 4-187695
Patent Document 3: Japanese Patent Application Laid-Open Publication No. 62-155082
Patent Document 4: Japanese Patent Application Laid-Open Publication No. 3-287594

Non-Patent Documents

Non-patent Document 1: Brazilian archives of biology and technology, 2010; 53(3): 719-729
Non-patent Document 2: Journal of Industrial Microbiology & Biotechnology, 2001; 26(5): 290-295

SUMMARY OF THE INVENTION

Problems to be Solved by the Invention

However, the purity of soybean oligosaccharide in a soybean oligosaccharide liquid obtained by conventional methods was low. Also, its handleability in solid-liquid separation, membrane treatment, fermentation, or the like was significantly poor. Since the soybean oligosaccharide liquid obtained by the conventional production method for soybean oligosaccharides contains suspended substances that are difficult to be separated, it was difficult to carry out membrane treatment using a separation membrane or the like. Further, stirring is difficult in cases where the soybean oligosaccharide liquid obtained by the conventional method is used as a fermentation raw material (a carbon source), as compared with the case in which a usual liquid medium is used, and thus there is thought to be a possibility of generating aggregated precipitates during fermentation or making purification of fermentation products difficult.

In light of such a situation, an object of the present invention is to provide a method for producing a purified soybean oligosaccharide liquid, the method being capable of producing a soybean oligosaccharide liquid with high purity and excellent handleability.

Means for Solving the Problems

In order to solve the above-mentioned problems, the present inventors have intensively studied on production methods for soybean oligosaccharides. As a result, it was found that a soybean oligosaccharide liquid with high purity and excellent handleability can be obtained by mixing cellulase into a soybean oligosaccharide suspension to promote aggregation precipitation of suspended substances that remain in the soybean oligosaccharide suspension, and thereafter removing the suspended substances in the soybean oligosaccharide suspension. The present invention has been attained based on such findings.

That is, a method for producing a purified soybean oligosaccharide liquid according to the present invention is a method for producing a purified soybean oligosaccharide liquid from a soybean and/or a processed soybean product, the method comprising: the step (1) of mixing the soybean and/or the processed soybean product with a water-containing polar organic solvent that contains a polar organic solvent and water and then removing a generated precipitate to obtain a soybean oligosaccharide liquid that contains the water-containing polar organic solvent; the step (2) of removing the polar organic solvent from the soybean oligosaccharide liquid to obtain a soybean oligosaccharide suspension; the step (3) of mixing the soybean oligosaccharide suspension with cellulase to obtain a cellulase-treated soybean oligosaccharide suspension; and the step (4) of subjecting the cellulase-treated soybean oligosaccharide suspension to solid-liquid separation to obtain a purified soybean oligosaccharide liquid.

In the present invention, it is preferred that the cellulase comprise one type or two or more types selected from the group consisting of: β-glucosidase, cellobiohydrolase, and endoglucanase.

In the present invention, it is preferred that the soybean oligosaccharide liquid be subjected to heating and/or pressure reduction to remove the polar organic solvent in the step (2).

In the present invention, it is preferred that the total solid concentration of the soybean oligosaccharide suspension be adjusted in a range of 10 to 35% (w/w) before mixing with the cellulase in the step (3).

In the present invention, it is preferred to comprise the step (5) of further purifying the purified soybean oligosaccharide liquid using one type or two or more types of separation membranes selected from the group consisting of: a microfiltration membrane, an ultrafiltration membrane, a nanofiltration membrane, and a reverse osmosis membrane.

In the present invention, it is preferred that the pH of the cellulase-treated soybean oligosaccharide suspension be adjusted in a range of 1.0 to 6.0 in the step (4).

In the present invention, it is preferred that an alkaline earth metal salt be mixed into the cellulase-treated soybean oligosaccharide suspension in the step (4).

In the present invention, it is preferred that esterase be further mixed into the soybean oligosaccharide suspension in the step (3).

In the present invention, it is preferred that ethanol be used as the polar organic solvent.

In the present invention, it is preferred that when the soybean and/or the processed soybean product are/is mixed with the water-containing polar organic solvent in the step (1), the concentration of polar organic solvent that is calculated by the following equation (I) be in a range of 50 to 90% (w/w).

Concentration of polar organic solvent=Mass of polar organic solvent in water-containing polar organic solvent/(Mass of water contained in soybean and/or processed soybean product+ Total mass of water-containing polar organic solvent)     (I)

A method for producing a chemical according to another mode of the present invention is characterized by producing a chemical using the purified soybean oligosaccharide liquid obtained by using any of the above methods for producing a purified soybean oligosaccharide liquid as a fermentation raw material.

Effect of the Invention

In the present invention, aggregation precipitation of suspended substances that remain behind in a soybean oligosaccharide suspension is promoted in the step (3), and the suspended substance in the cellulase-treated soybean oligosaccharide suspension is subjected to solid-liquid separation to remove in advance the suspended substance from the soybean oligosaccharide suspension in the step (4). Therefore, according to the present invention, a soybean oligosaccharide liquid with high purity and excellent handleability can be produced from a soybean and/or a processed soybean product. Thus, the purified soybean oligosaccharide liquid can be readily subjected to membrane separation and, when used as a fermentation raw materials, can be readily stirred. Besides, fermentation products can be more readily purified with no aggregation precipitation occurring.

MODE FOR CARRYING OUT THE INVENTION

Modes for carrying out the present invention will be described in detail below.

<Method for Producing Purified Soybean Oligosaccharide Liquid>

Each of the steps of the method for producing a purified soybean oligosaccharide liquid according to the present invention will be described.

[Step (1): Recovery of Soybean Oligosaccharide by Polar Organic Solvent]

In the step (1), a soybean and/or a processed soybean product are/is added to a water-containing polar organic solvent that contains a polar organic solvent and water; the soybean and/or the processed soybean product are/is mixed with the water-containing polar organic solvent that contains the polar organic solvent and water. Thus, a precipitate with a protein derived from the soybean and/or the processed soybean product as a major component is formed in the water-containing polar organic solvent.

It is to be noted that, in the present specification, soybeans refer to raw soybeans and may be either of soybeans with skin or soybeans from which skin has been removed. Also, soybeans may be ground in advance. Any processed soybean product may be used as long as it contains soybean oligosaccharides. Preferably used are, for example, ones obtained by immersing soybeans in water, soy milk obtained by subjecting soybeans to extraction with hot water, okara (soybeans pulp) which is a solid residue when soybeans are subjected to extraction with hot water, soybean whey obtained by precipitating and removing proteins and the like from soy milk by acid precipitation, defatted soybeans which is residues obtained by extracting and removing lipids from soybeans by solvent extraction, and the like. In addition, an oligosaccharide is a compound in which 2 to 10 monosaccharides are linked by a glycosidic bond. In addition, a soybean oligosaccharide is a general term for oligosaccharides that are contained in soybeans; it mainly includes and is composed of sucrose, raffinose, stachyose, and the like. A soybean oligosaccharide liquid refers to a solution that contains soybean oligosaccharides.

A water-containing polar organic solvent refers to a solution mixture of the above polar organic solvent and water. Any polar organic solvent may be used as long as it is capable of dissolving soybean oligosaccharides and does not dissolve most proteins; what can be used as the polar organic solvent is, for example, ethanol, methanol, acetone, acetonitrile, propanol, butanol, isobutanol, propanediol, butanediol, or the like. Considering the soybean oligosaccharide is used for food product application or the like, it is particularly preferred to use ethanol as the polar organic solvent.

When a soybean and/or a processed soybean product are/is mixed with a water-containing polar organic solvent, the concentration of the polar organic solvent is calculated by the equation (I).

$$\text{Concentration of polar organic solvent} = \text{Mass of polar organic solvent in water-containing polar organic solvent}/(\text{Mass of water/moisture in soybean and/or processed soybean product} + \text{Total mass of water-containing polar organic solvent}) \quad (I)$$

It is preferred that the concentration of polar organic solvent, which concentration is calculated by the above equation (I), be in a range of 50 to 90% (w/w). That is because, in cases where the concentration of polar organic solvent is not more than 90% (w/w), deposition and precipitation of soybean oligosaccharides can be inhibited and, in cases where the concentration of polar organic solvent is not less than 50% (w/w), precipitates of impurities composed mainly of proteins are sufficiently formed.

As regards the amount of the water-containing polar organic solvent added, the added amount at which the concentration of soybean oligosaccharides in a soybean oligosaccharide liquid that contains a water-containing polar organic solvent, which is described later (hereinafter, referred to also as "polar organic solvent-containing oligosaccharide liquid"), is preferably in a range of 1 to 30% (w/w) and more preferably in a range of 10 to 25% (w/w). In cases where the concentration of soybean oligosaccharides in a polar organic solvent-containing oligosaccharide liquid is not less than 1% (w/w), energy or costs for concentrating the soybean oligosaccharide in the subsequent steps can be reduced. Further, in cases where the concentration of soybean oligosaccharides in a polar organic solvent-containing oligosaccharide liquid is not more than 30% (w/w), deposition and precipitation of soybean oligosaccharides can be inhibited and a decrease in the yield of soybean oligosaccharides can be inhibited. It is to be noted that the concentration of soybean oligosaccharides can be measured using a conventionally known device and can for example be quantified and determined by comparison with a standard sample using high performance liquid chromatography (HPLC).

Further, in the present specification, the concentration of soybean oligosaccharides refers to, unless otherwise noted, a sum of the concentrations of sucrose, raffinose, and stachyose.

A mixing time of a soybean and/or a processed soybean product with a water-containing polar organic solvent is preferably one minute to 10 hours and most preferably 10 minutes to three hours. If the mixing time is not less than one minute, precipitates of impurities composed mainly of proteins are sufficiently formed. Also, a 10-hour mixing time is enough to maximize the precipitation amount of impurities composed mainly of proteins, and an extra time can be cut down.

A temperature at the time of mixing a soybean and/or a processed soybean product with a water-containing polar organic solvent is preferably 10° C. to 90° C. and more preferably 20° C. to 40° C. In cases where the temperature at the time of the mixing is not less than 10° C., deposition of soybean oligosaccharides in the water-containing polar organic solvent can be inhibited. Further, in cases where the temperature at the time of the mixing is not more than 90° C., breakdown of oligosaccharides can be inhibited. In addition, in cases where the temperature at the time of the mixing is not more than 90° C., possibility of browning by Maillard reaction is able to be lowered.

Next, after mixing of a soybean and/or a processed soybean product with a water-containing polar organic solvent, a water-containing polar organic solvent that contains soybean oligosaccharides and a precipitate formed in the water-containing polar organic solvent are subjected to solid-liquid separation to remove the precipitate.

A method for solid-liquid separation is not particularly restricted; a conventionally known common method for solid-liquid separation can be used. Examples of the method for solid-liquid separation include centrifugation, filter pressing, belt filter, separation by spontaneous sedimentation, filtration by mesh screen, filtration by non-woven fabric, and filtration by filter paper. A method for solid-liquid separation between a polar organic solvent and a precipitate may be used alone and plural methods may be used in combination. Of those, filter pressing is most preferably used, from the point of view that particulate solids can be efficiently removed and a larger amount of polar organic solvent-containing oligosaccharide liquid can be recovered by compressing the solid removed.

After removal of a precipitate from a polar organic solvent that contains soybean oligosaccharides using a method for solid-liquid separation, an oligosaccharide liquid that contains a polar organic solvent (polar organic solvent-containing oligosaccharide liquid) is recovered.

[Step (2): Removal of Polar Organic Solvent]

In the step (2), a polar organic solvent is removed from the polar organic solvent-containing soybean oligosaccharide liquid recovered in the above step (1) to obtain a soybean oligosaccharide suspension.

As a method for removing a polar organic solvent from a polar organic solvent-containing soybean oligosaccharide liquid, a method comprising heating and/or reducing pressure of a polar organic solvent-containing oligosaccharide liquid and evaporating a polar organic solvent for removal is suitably used. A device used in a method of evaporating the polar organic solvent for removal is not particularly restricted; what can be used are, for example, an evaporator, a heat evaporator, an effect evaporator, a multiple effect evaporator, and the like can for example be used.

It is preferred that a temperature when a polar organic solvent is evaporated be in a range of 10 to 60° C. This is because the amount of polar organic solvent evaporated is sufficient at not less than 10° C. and the possibility to cause browning by Maillard reaction can be lowered at not more than 60° C.

Any concentration of polar organic solvent that remains behind in a soybean oligosaccharide suspension may be employed as long as enzymes are not inhibited or deactivated in the step (3) described later; the concentration is preferably not more than 10% (vol/vol) and more preferably not more than 1% (vol/vol).

Further, in cases where a polar organic solvent is removed from a polar organic solvent-containing soybean oligosaccharide liquid by evaporation in this step, the evaporated polar organic solvent is able to be recovered in a cold trap or the like and can again be reused as the polar organic solvent in the step (1).

As compared with soybean whey and the like, the soybean oligosaccharide suspension obtained in this step has reduced amounts of proteins and lipids and can also be said to be a partially purified liquid of soybean oligosaccharides. However, since the purity of soybean oligosaccharides is still low and suspended substances that are difficult to be separated are contained, it is difficult to apply methods of purifying or concentrating the soybean oligosaccharide suspension using membrane filtration or the like. In view of this, the suspended substance in the soybean oligosaccharide suspension is further removed by the step (3) and step (4) described below in the present invention.

It is to be noted that a value obtained by, according to the following equation (1), dividing the total value (g) of the mass of each oligosaccharide such as sucrose, raffinose, or stachyose by the mass (g) of the total solids (hereinafter, referred to also as TS) in an aqueous solution is regarded as the soybean oligosaccharide purity in the present invention. It is to be noted that total solids correspond to residues after evaporation.

$$\text{Oligosaccharide purity (\%)} = \text{Total value (g) of mass of each oligosaccharide (sucrose, raffinose, stachyose)/Mass (g) of total solids} \quad (1)$$

[Step (3): Cellulase Treatment of Soybean Oligosaccharide Suspension]

In the step (3), cellulase is mixed into the soybean oligosaccharide suspension obtained in the step (2), and the soybean oligosaccharide suspension is subjected to cellulase treatment, thereby obtaining a cellulase-treated soybean oligosaccharide suspension. In the step (3), by allowing cellulase to act on impurities in the soybean oligosaccharide suspension, it is possible to promote aggregation precipitation of suspended substances that remain behind in the soybean oligosaccharide suspension. It is to be noted that, in the present specification, mixing cellulase into the soybean oligosaccharide suspension followed by allowing cellulase to act on the impurities in the soybean oligosaccharide suspension is called cellulase treatment.

In the soybean oligosaccharide suspension obtained in the above-mentioned step (2), in addition to the soybean oligosaccharide, a variety of impurities are contained. As the impurities, lipids are most abundantly contained and, next to that, amphipathic substances such as saponin, isoflavone, and lecithin are contained. Also, the soybean oligosaccharide suspension further contains a very small amount of proteins. Since these impurities such as the lipids, amphipathic substances, and proteins multiply act to form very stable micellar suspended substances in the soybean oligosaccharide suspension, it is difficult to separate these impurities from oligosaccharides. In the present invention, it is possible to promote aggregation precipitation of the suspended substance that remains behind in the soybean oligosaccharide suspension by adding cellulase to the soybean oligosaccharide suspension, mixing them and allowing cellulase to act on the impurities in the soybean oligosaccharide suspension in this step. Because of this, it is possible to remarkably improve performance of solid-liquid separation between the soybean oligosaccharide and the suspended substance in the soybean oligosaccharide suspension. This is thought to be, for example, because carbohydrate chains in saponin or isoflavone in the impurities are broken down by cellulase so that the impurities lose their property as an amphipathic substance.

It is to be noted that, in the present invention, cellulase is a general term for enzymes that catalyze the hydrolysis of a β-glucoside bond in a carbohydrate chain and refers to an enzyme or an enzymatic agent that contains one type or two or more types of components selected from the group consisting of: β-glucosidase, cellobiohydrolase, and endoglucanase.

β-glucosidase refers to an enzyme having an activity of hydrolyzing cellobiose. An activity of breaking down cellobiose (hereinafter, referred to also as "BGL activity") can be measured based on the amount of glucose released when the enzyme is allowed to act on cellobiose as a substrate. The BGL activity can be measured according to, for example, a method for "Cellobiase assay" described in "Pure & Appl. Chem., Vol. 59, No. 2, pages 257-268". To be specific, the activity can be measured, for example, under reaction conditions of 50° C. and pH 5.0 and calculated as BGL activity per one mL of enzyme liquid (the unit is U/mL) or the like. It is to be noted that, in the present invention, one unit (U) of BGL activity is defined as an "enzymatic activity that breaks down one μmol of cellobiose in a cellobiose breakdown reaction for one minute (or generates two μmol of glucose for one minute)".

Further, in the present invention, even when an enzyme is in general classified as other enzymes such as β-galactosidase, if the enzyme has the above BGL activity, it shall be regarded as one type of β-glucosidase.

Cellobiohydrolase refers to an enzyme having an activity of breaking down crystalline cellulose from the terminal end. An activity of breaking down crystalline cellulose can be measured based on the amount of glucose released when the enzyme is allowed to act on crystalline cellulose as a substrate. As a specific method for measuring the activity of breaking down crystalline cellulose, a method described in "FILTER PAPER ASSAY FOR SACCHARIFYING CELLULASE" in "Pure & Appl. Chem., Vol. 59, No. 2, pages 257-268" or the like can be used.

Endoglucanase refers to an enzyme having an activity of cleaving noncrystalline cellulose from the center. An activity of breaking down noncrystalline cellulose can be measured based on the amount of reducing sugars released when the enzyme is allowed to act on carboxymethylcellulose (CMC) as a substrate. As a specific method of measuring the activity of breaking down noncrystalline cellulose, a method described in "CARBOXYL CELLULASE ASSAY FOR ENDO-β-1,4-GLUCANASE" in "Pure & Appl. Chem., Vol. 59, No. 2, pages 257-268" or the like can be used.

When the amounts of cellulases used in the present invention are made even so that their amounts of proteins are equalized, the higher a β-glucosidase specific activity (BGL specific activity) is, the higher an effect of promoting aggregation precipitation of suspended substances is. It is to be noted that the BGL specific activity refers to a BGL activity per amount of proteins contained in an enzymatic agent. In the present invention, the BGL specific activity is calculated as a value obtained by dividing a measurement value (U/mL) of BGL activity per one mL of enzyme liquid by a value of the concentration (mg/mL) of proteins in an enzyme liquid measured by Bradford method (the unit is U/mg).

It is preferred that the BGL specific activity of the cellulase used in the present invention be, for example, not less than one U/mg. If the BGL specific activity of cellulase is not less than one U/mg, it is possible to make an effect of promoting aggregation precipitation of suspended substances sufficiently high.

Further, in the present invention, when a purified product that contains β-glucosidase alone is compared with a cellulase preparation that contains, in addition to β-glucosidase, other components such as cellobiohydrolase or endoglucanase, even when the BGL activity is the same, the cellulase preparation that contains β-glucosidase and other components exhibits a much higher effect of promoting aggregation precipitation of suspended substances. This is presumably because β-glucosidase and other cellulase components concertedly work to enhance the effect in the step (3).

In the present invention, since an effect of promoting aggregation precipitation of suspended substances comes to the highest level when the pH at the time of cellulase treatment is the optimum pH of enzyme, it is preferred to adopt the optimum pH of enzyme as the pH at the time of cellulase treatment. It is to be noted that, since the optimum pH of cellulase preparation is usually about 4 to 6 and the pH of the suspension obtained through the above-mentioned process is usually about 4.5 to 5.5, pH adjustment just may be carried out as appropriate only if necessary.

In the present invention, the temperature of soybean oligosaccharide suspension at the time of cellulase treatment is preferably set to the optimum temperature of cellulase to be used. The optimum temperature of cellulase is around 50° C. in many cases, and is preferably adjusted as appropriate according to the type of cellulase to be used.

In the present invention, the total solid concentration (TS concentration) in a soybean oligosaccharide suspension is preferably adjusted in a range of 10 to 35% (w/w) before mixing of cellulase. If the total solid concentration is not more than 35% (w/w), aggregation precipitation of suspended substances is sufficiently promoted, which enables the necessary amount of cellulase added to be reduced. This is thought to be because, by adjusting the total solid concentration to not more than 35% (w/w), the water activity of the soybean oligosaccharide suspension is enhanced whereby the activity of cellulase improves. Further, if the total solid concentration is not less than 10% (w/w), a decrease in the concentration of oligosaccharides that is eventually attained can be reduced.

It is to be noted that TS concentration is a value obtained by dividing the mass of total solids (TS) in an aqueous solution by the mass of total aqueous solution (the unit is % (w/w)). Further, the mass of TS in an aqueous solution can be measured by using a conventionally known device such as an infrared moisture determination balance (FD-720, manufactured by Kett).

In the present invention, the amount of cellulase added and the period of time for cellulase treatment are not particularly restricted and may be only required to be adjusted so that aggregation precipitation of suspended substances is sufficiently promoted. In general, if the amount of cellulase added is increased, the cost of cellulase increases, but the period of time necessary for the treatment is shortened, and thus the costs of equipment can be reduced. On the other hand, if the amount of cellulase added is decreased, the cost of cellulase can decrease, but the period of time necessary for the treatment becomes longer, and thus the costs of equipment increase. Because of this, it is preferred that the amount of cellulase added and the period of time for the treatment be appropriately adjusted depending on the situation including production schedule for soybean oligosaccharides.

In the step (3) of the present invention, it is preferred to further mix esterase with a soybean oligosaccharide suspension at the time of the cellulase treatment. By adding also esterase to a soybean oligosaccharide suspension, aggregation precipitation of suspended substances can be still more significantly promoted. This is presumably because an ester bond is broken down by esterase, the ester bond being present in a carbohydrate chain part of lecithin, saponin, or isoflavone which is contained in the soybean oligosaccharide suspension. The kind of esterase is not particularly restricted; lipase which can be industrially used at a relatively low price or the like is suitably used.

[Step (4): Recovery of Purified Soybean Oligosaccharide Liquid]

In the step (4) of the present invention, the cellulase-treated soybean oligosaccharide suspension obtained in the above step (3) is subjected to solid-liquid separation to remove the suspended substances obtained by the aggregation precipitation in the soybean oligosaccharide suspension in the step (3), thereby obtaining a purified soybean oligosaccharide liquid. This obtained purified soybean oligosaccharide liquid exhibits high oligosaccharide purity, low turbidity, and a high filtration rate upon passage through a filtration membrane; therefore the purified soybean oligosaccharide liquid exhibits high purity and excellent handleability.

A method for solid-liquid separation is not particularly restricted; the same method for solid-liquid separation as described in the above step (1) can be used. Of those, preferred is centrifugation and, in particular, most preferred is use of a continuous centrifuge capable of continuously carrying out recovery of the supernatant of cellulase-treated soybean oligosaccharide suspension. As the continuous centrifuge, a screw decanter, a De Laval-type centrifuge, and the like are suitably used.

The pH of cellulase-treated soybean oligosaccharide suspension when a cellulase-treated soybean oligosaccharide suspension is subjected to solid-liquid separation is preferably in a range of 1.0 to 6.0 and further preferably 2.0 to 3.0. In cases where the pH of cellulase-treated soybean oligosaccharide suspension is not less than 1.0, hydrolysis of oligosaccharides is hard to take place. On the other hand, in cases where the pH of cellulase-treated soybean oligosaccharide suspension is not more than 6.0, the solid-liquid separation of the cellulase-treated soybean oligosaccharide suspension can be carried out well, which is thus preferred. Further, an oligosaccharide liquid that has still more significant clarity and is easily subjected to membrane filtration can be obtained by carrying out the solid-liquid separation in a range of pH 2 to 3; it is therefore most preferred to set the pH in a range of 2 to 3. It is to be noted that because the pH of the cellulase-treated soybean oligosaccharide suspension obtained in the above step (3) is usually about 4.5 to 5.5, pH adjustment may be only required to be carried out as necessary.

An acid or an alkali used in pH adjustment of a cellulase-treated soybean oligosaccharide suspension is not particularly restricted. Examples of the acid include hydrochloric acid, sulfuric acid, nitric acid, and phosphoric acid. Preferred are sulfuric acid, nitric acid, and phosphoric acid from the point of view that inhibition at the time of fermentation is hard to occur; more preferred is sulfuric acid from the point of view of economic efficiency. As the alkali, preferred are ammonia, sodium hydroxide, calcium hydroxide, and an aqueous solution containing those from the point of view of economic efficiency; more preferred are ammonia and sodium hydroxide which are monovalent ions from the point of view of membrane fouling; still more preferred is ammonia from the point of view that inhibition at fermentation is hard to occur.

Adjustment of the pH of cellulase-treated soybean oligosaccharide suspension may be carried out immediately before solid-liquid separation or at the same time as the solid-liquid separation. The cellulase-treated soybean oligosaccharide suspension can be subjected to the adjustment of pH before the solid-liquid separation and left to stand for a certain period of time until the solid-liquid separation is started, thereby further enhancing effects. An exemplary method involves carrying out the solid-liquid separation after the pH of cellulase-treated soybean oligosaccharide suspension is adjusted and is left to stand for one hour.

In the present invention, it is preferred that an alkaline earth metal salt be added to a cellulase-treated soybean oligosaccharide suspension. By mixing the alkaline earth metal salt before or at the same time as solid-liquid separation of the cellulase-treated soybean oligosaccharide suspension, a purified soybean oligosaccharide liquid with still more clarity can be obtained. This is presumably because fatty acid salts in the cellulase-treated soybean oligosaccharide suspension exchange cations with the alkaline earth metal to form insoluble salts. By obtaining the purified soybean oligosaccharide liquid with still more clarity, a filtration rate when the purified soybean oligosaccharide liquid is subjected to the membrane filtration can further be improved.

As an alkaline earth metal salt, calcium carbonate, calcium chloride, and the like can preferably be used. Further, the concentration of alkaline earth metal added is not particularly restricted; the final concentration of alkaline earth metal salt in a cellulase-treated soybean oligosaccharide suspension after the addition of the alkaline earth metal salt is preferably in a range of 5 to 20 g/L. In cases where the final concentration of alkaline earth metal salt in the cellulase-treated soybean oligosaccharide suspension is not less than 5 g/L, impurities are sufficiently removed; in cases where the final concentration in the cellulase-treated soybean oligosaccharide suspension is not more than 20 g/L, effects corresponding to the added alkaline earth metal are sufficiently attained and an increase in reagent costs can concurrently be suppressed, which is thus economically preferred.

In this way, the method for producing a purified soybean oligosaccharide liquid according to the present invention comprises the above step (1) to step (4); a purified soybean oligosaccharide liquid with high purity and clarity can be obtained by promoting aggregation precipitation of suspended substances that remain behind in the soybean oligosaccharide suspension in the step (3) and by removing the suspended substance in the cellulase-treated soybean oligosaccharide suspension in the step (4).

Since the purified soybean oligosaccharide liquid obtained in the step (4) is a soybean oligosaccharide liquid with clarity that hardly contains suspended substances, membrane separation can be readily carried out. Further, in cases where the purified soybean oligosaccharide liquid obtained in the step (4) is used as a fermentation raw material, the purified soybean oligosaccharide liquid can be readily stirred and fermentation products are also readily further purified with no aggregation precipitation occurring. Thus, by virtue of the method for producing a purified soybean oligosaccharide liquid according to the present invention, it is possible to produce a soybean oligosaccharide liquid with high purity and excellent handleability from a soybean and/or a processed soybean product.

Further, when compared with the soybean oligosaccharide suspension obtained in the step (2) or the cellulase-treated soybean oligosaccharide suspension obtained in the step (3) as a fermentation raw material, the purified soybean oligosaccharide liquid obtained in the step (4) makes it possible to increase a growth rate of microorganisms or a production rate and accumulation concentration of chemicals. This is thought to be because some sort of substances that inhibit the proliferation and metabolism of microorganisms (hereinafter, referred to also as fermentation inhibitors), which substances are contained in suspended substances in the cellulase-treated soybean oligosaccharide suspension, are removed from the cellulase-treated soybean oligosaccharide suspension in the step (4).

The purified soybean oligosaccharide liquid obtained in the step (4) can be used as is in a variety of applications including food raw materials, pharmaceutical product raw materials, and fermentation raw materials (carbon sources) in fermentation production of fermentation products such as chemicals by microorganisms and can improve efficiency in the production of these food products, pharmaceutical products, and fermentation products such as chemicals by microorganisms. Examples of the chemical include alcohols such as ethanol, propanol, and butanol; acetic acid; lactic acid; and amino acids. In addition, the purified soybean oligosaccharide liquid can be processed into powdery oligosaccharides by evaporating water of the purified soybean oligosaccharide liquid. Further, the purified soybean oligosaccharide liquid can also be readily subjected to membrane filtration and can therefore be used also as a raw material for producing a more highly purified soybean oligosaccharide.

Further, by allowing an enzyme such as α-galactosidase, invertase, or sucrase to act on the purified soybean oligosaccharide liquid obtained in the step (4), a soybean oligosaccharide can be broken down into monosaccharides such as galactose, glucose, or fructose. The obtained monosaccharide can be used in sugar raw materials. The sugar raw material can suitably be used in food products, feeds, and fermentation raw materials in fermentation production of chemicals by microorganisms, and the like. It is to be noted that, in the above fermentation production of chemicals by microorganisms, the breakdown from the oligosaccharide to the monosaccharide by the above enzyme can be carried out before or at the same time as the fermentation production.

[Other Step]

(Step (5): Further Purification of Purified Soybean Oligosaccharide Liquid by Membrane Filtration)

As described above, the present invention can comprise the step (5) of filtering the purified soybean oligosaccharide liquid obtained in the step (4) for further purification. As a separation membrane used in the filtration for further purification of the purified soybean oligosaccharide liquid, a microfiltration membrane, an ultrafiltration membrane, a nanofiltration membrane, a reverse osmosis membrane, and the like are used. As for the membrane used in the filtration, one kind of those may be solely used, or two or more kinds may be used in combination. In cases where the microfiltration membrane is used, particulate impurities with a size of microns can be removed from the purified soybean oligosaccharide liquid. Further, in cases where the ultrafiltration membrane is used, high molecular weight impurities such as proteins can be removed. Further, in cases where the nanofiltration membrane or the reverse osmosis membrane is used, part of low molecular weight impurities can be removed and, at the same time, the soybean oligosaccharide can be concentrated.

The soybean oligosaccharide suspension obtained in the step (2) of the present invention and the cellulase-treated soybean oligosaccharide suspension obtained in the step (3) exhibit poor membrane filterability and immediately cause clogging of the above various filtration membranes; therefore purification by membrane filtration using the above various filtration membranes is very difficult. By contrast, the purified soybean oligosaccharide liquid obtained in the present invention exhibits good membrane filterability; therefore particles with a size of microns, high molecular weight molecules, ions, and the like can be removed by treatment through the above separation membrane to obtain a more highly purified soybean oligosaccharide liquid with high clarity.

Examples of a method for filtration include pressure filtration, vacuum filtration, and centrifugal filtration; the method is not particularly restricted. Further, filtration operation is roughly divided into constant pressure filtration, constant flow rate filtration, and non-constant pressure non-constant flow rate filtration, and is not particularly restricted. Further as for filtration operation, multistage filtration using any of the above separation membranes twice or more may be employed; materials and properties of the membrane at that time are not particularly restricted.

Further, in cases where a purified soybean oligosaccharide liquid is filtered using any one or more of an ultrafiltration membrane, a nanofiltration membrane, and a reverse osmosis membrane, it is preferred to pass the purified soybean oligosaccharide liquid through a microfiltration membrane in advance. When the purified soybean oligosaccharide liquid is passed through an ultrafiltration membrane, a nanofiltration membrane, and a reverse osmosis membrane, clogging of these membranes can be suppressed by preliminary treatment of the purified soybean oligosaccharide liquid by passing the purified soybean oligosaccharide liquid through a microfiltration membrane to remove micron-size particles contained in the purified soybean oligosaccharide liquid.

Further, in cases where a purified soybean oligosaccharide liquid is filtered using a nanofiltration membrane and/or a reverse osmosis membrane, it is preferred to pass the purified oligosaccharide liquid through an ultrafiltration membrane in advance. When the purified soybean oligosaccharide liquid is passed through a nanofiltration membrane and/or a reverse osmosis membrane, clogging of these membranes can be suppressed by preliminary treatment of the purified soybean oligosaccharide liquid by passing the purified soybean oligosaccharide liquid through an ultrafiltration membrane to remove high molecular weight components such as proteins that are contained in the purified soybean oligosaccharide liquid.

It is to be noted that the microfiltration membrane used in the present invention refers to a membrane with an average fine pore diameter of 0.01 µm to 10 µm and is abbreviated as an MF (microfiltration) membrane, or the like. In addition, an ultrafiltration membrane used in the present invention is a membrane with a molecular weight cut off of 1,000 to 200,000 and is abbreviated as a UF (Ultrafiltration) membrane, or the like. Here, the pore diameter of the ultrafiltration membrane is so small that it is difficult to measure the fine pore diameter on the membrane surface by an electron microscope or the like; a value termed as molecular weight cut off, instead of the average fine pore diameter, has been used as an index for the size of pore diameter. The molecular weight cut off refers to one that is well known to those skilled in the art as an index representing the membrane performance of ultrafiltration membrane, as is described that "a curve obtained by plotting data with the molecular weight of the solute along the horizontal axis and the blocking rate along the vertical axis is called a molecular weight cut off curve; the molecular weight at which the blocking rate is 90% is called the molecular weight cut off of the membrane." in The Membrane Society of Japan ed., Membrane Experiment Series, Vol. III, Artificial Membrane, edited by Shoji Kimura, Shin-ichi Nakao, Haruhiko Ohya, and Tsutomu Nakagawa (1993 Kyoritsu Shuppan Co., Ltd.), page 92.

Materials of these microfiltration membranes or ultrafiltration membranes are not particularly restricted as long as the material can attain the aforementioned object of the present invention of removing fine particles; examples thereof include organic materials such as cellulose, cellulose esters, polysulfone, polyether sulfone, chlorinated polyethylene, polypropylene, polyolefin, polyvinyl alcohol, polymethylmethacrylate, polyvinylidene fluoride, or polyethylene tetrafluoride, metals such as stainless steel, and inorganic materials such as ceramic. The material of the microfiltration membrane or the ultrafiltration membrane may be selected as appropriate in the light of the characteristics of hydrolysate or running costs. It is preferably an organic material; chlorinated polyethylene, polypropylene, polyvinylidene fluoride, polysulfone, or polyether sulfone is preferred.

Further, filtration using a microfiltration membrane and an ultrafiltration membrane can be carried out according to, for example, a method described in WO 2010/067785.

The nanofiltration membrane used in the present invention is also called an NF membrane and is a separation membrane that is in general defined as a "membrane permeating monovalent ions whereas blocking divalent ions". The nanofiltration membrane is a membrane that is thought to have microscopic openings of about several nanometers and mainly used for blocking fine particles or molecules, ions, salts, or the like in water.

As materials that form the nanofiltration membrane, polymer materials such as cellulose acetate-based polymers, polyamides, polyesters, polyimides, or vinyl polymers can be used; the membrane is not limited to a membrane composed of one kind of the above-mentioned material and may be a membrane containing plural membrane materials. Further, with regard to the membrane structure of the nanofiltration membrane, the membrane may be either an asymmetric membrane which has a dense layer on at least one side and micropores having pore sizes that gradually increase in the direction from the dense layer toward the inside of the membrane or the other side of the membrane, or a composite membrane which has a very thin functional layer formed by another material on the dense layer of an asymmetric membrane. As the composite membrane, a composite membrane that has a nanofilter composed of a polyamide functional layer on a support membrane comprising polysulfone as a membrane material can be for example used. Such a composite membrane is described in, for example, Japanese Patent Application Laid-Open Publication No. 62-201606 or the like.

Of those, preferred is a composite membrane with a polyamide as a functional layer that exhibits high pressure resistance, high water permeability, and high solute removal performance in combination and having excellent potential. In order to be able to keep durability against operating pressure, high water permeability, and blocking performance, what is appropriate is one having a polyamide as a functional layer and a structure that retains the functional layer with a support composed of a porous membrane or a non-woven fabric. Also as a polyamide semipermeable membrane, a composite semipermeable membrane is appropriate, which composite semipermeable membrane has, as a support, a cross-linked polyamide functional layer obtained by a polycondensation reaction between a polyfunctional amine and a polyfunctional acid halide.

In a nanofiltration membrane with a polyamide as a functional layer, preferred examples of a carboxylic acid component of a monomer composed of a polyamide include aromatic carboxylic acids such as trimesic acid, benzophenone tetra carboxylic acid, trimellitic acid, pyromellitic acid, isophthalic acid, terephthalic acid, naphthalene dicarboxylic acid, diphenyl carboxylic acid, and pyridinecarboxylic acid. Considering the solubility in a membrane-forming solvent, more preferred are trimesic acid, isophthalic acid, terephthalic acid, and a mixture thereof.

Preferred examples of an amine component of the monomer composed of apolyamide include primary diamines having an aromatic ring such as m-phenylenediamine, p-phenylenediamine, benzidine, methylenebisdianiline, 4,4'-diaminodiphenyl ether, dianisidine, 3,3',4-triaminodiphenyl ether, 3,3',4,4'-tetraaminodiphenyl ether, 3,3'-dioxybenzidine, 1,8-naphthalenediamine, m(p)-monomethyl phenylenediamine, 3,3'-monomethylamino-4,4'-diaminodiphenyl ether, 4, N, N'-(4-aminobenzoyl)-p(m)-phenylenediamine-2,2'-bis(4-aminophenyl benzoimidazole), 2,2'-bis(4-aminophenyl benzoxazole), and 2,2'-bis(4-aminophenyl benzothiazole), and secondary diamines such as piperazine, piperidin, or derivatives thereof. Of these, a nanofiltration membrane with, as a functional layer, a cross-linked polyamide containing piperazine or piperidin as a monomer is preferably used since it has, in addition to pressure resistance and durability, thermal resistance and chemical resistance. More preferred is a polyamide that has a cross-linked piperazine polyamide or a cross-linked piperidin polyamide as a major component and contains a constituting component shown in the following chemical formula (i). Still more preferred is a polyamide that has a cross-linked piperazine polyamide as a major component and contains a constituting component shown in the following chemical formula (i). Also, one with n=3 in the following chemical formula (i) is preferably used. Examples of a nanofiltration membrane with, as a functional layer, a polyamide that has a cross-linked piperazine polyamide as a major component and contains a constituting component shown in the following chemical formula (i) include one described in Japanese Patent Application Laid-Open Publication No. 62-201606; specific examples thereof include a cross-linked piperazine polyamide-based nanofiltration membrane, UTC60 manufactured by Toray Industries, Inc., which has, as a functional layer, a polyamide that has a cross-linked piperazine polyamide as a major component and contains one with n=3 in the following chemical formula (i) as a constituting component.

(i)

(n is an integer that is not less than 1.)

Nanofiltration membranes are in general used as a spiral-type membrane module; the nanofiltration membrane used in the present invention is also preferably used as a spiral-type membrane module. Specific examples of a preferred nanofiltration membrane module include: (a) a nanofiltration membrane manufactured by GE Osmonics, GEsepa, which is a cellulose acetate-based nanofiltration membrane; (b) a nanofiltration membrane manufactured by Alfa Laval, NF99 or NF99HF, which has a polyamide as a functional layer; (c) a nanofiltration membrane manufactured by Filmtec, NF-45, NF-90, NF-200, NF-270, or NF-400, which has cross-linked piperazine polyamide as a functional layer; and (d) a nanofiltration membrane module manufactured by Toray Industries, Inc., SU-210, SU-220, SU-600, or SU-610, which contains UTC-60 manufactured by the same manufacturer, which UTC-60 has, as a functional layer, a polyamide that has a cross-linked piperazine polyamide as a major component and contains a constituting component shown in the above-mentioned chemical formula (i). More preferred is the above membrane (b), (c), or (d); still more preferred is the above (d) membrane.

It is preferred that the pH of purified soybean oligosaccharide liquid to be subjected to nanofiltration membrane be in a range of pH 1 to 5. This is because in cases where the pH is not less than 1, it is possible to suppress a significant deterioration of membrane performance such as flux or permeability caused by membrane denaturation upon long-term use; in cases where the pH is not more than 5, it is possible to suppress a significant decrease in a removal rate of substances that inhibit proliferation and metabolism of microorganisms, that is, fermentation inhibitors. For that reason, by adjusting the pH of the purified soybean oligosaccharide liquid within the above range and carrying out filtration with a nanofiltration membrane, an efficiency of removing the fermentation inhibitor can be improved. Also, when the pH of the purified soybean oligosaccharide liquid is within the above range, the nanofiltration membrane can be stably used for a long period of time because of an effect of reducing fouling of the nanofiltration membrane.

The temperature of a purified soybean oligosaccharide liquid that is passed through a nanofiltration membrane can be appropriately set from the point of view of increasing an ability of the nanofiltration membrane employed to remove fermentation inhibitors at the time of filtration. To be specific, in cases where the filtration is carried out with the nanofiltration membrane, if the temperature of purified soybean oligosaccharide liquid is 40° C. to 80° C., nanofiltration membrane's performance in removing the fermentation inhibitor is enhanced, which is therefore preferred. In cases where the temperature of the purified soybean oligosaccharide liquid when the filtration is carried out with the nanofiltration membrane is not less than 40° C., the performance in removing the fermentation inhibitor contained in the purified soybean oligosaccharide liquid increases; in cases where the temperature of the purified soybean oligosaccharide liquid is not more than 80° C., denaturation of the nanofiltration membrane can be inhibited and therefore membrane properties can be maintained. Because of this, by setting the temperature of purified soybean oligosaccharide liquid within the above range, nanofiltration membrane's performance in removing the fermentation inhibitor can be improved.

Further, to be specific, nanofiltration can be carried out according to, for example, a method described in WO 2010/067785.

In cases where a purified soybean oligosaccharide liquid is filtered using a nanofiltration membrane, fermentation inhibitors can be more efficiently removed by adding water to the purified soybean oligosaccharide liquid. Also, the amount of water added can be used to control the content of the fermentation inhibitors contained in the purified sugar liquid after nanofiltration. To be specific, the more the amount of water added is, the less the content of the fermentation inhibitor contained in a purified sugar liquid after the nanofiltration is.

The reverse osmosis membrane used in the present invention is also called an RO membrane and is in general defined as a "membrane having a function of removing salts including monovalent ions". The membrane is thought to have microscopic openings ranging from about several angstroms to several nanometers and mainly used for removal of ion components, for example, desalination of sea water or production of ultrapure water.

Further, filtration using a reverse osmosis membrane can be carried out according to, for example, a method described in WO 2010/067785.

In this way, further purification of the purified soybean oligosaccharide liquid obtained in the step (4) using any one or more of the above separation membranes in the step (5) makes it possible to obtain a purified soybean oligosaccharide liquid that is further purified and has high purity and high clarity.

EXAMPLES

For the purpose of more detailed description, the method for producing a purified soybean oligosaccharide liquid according to the present invention will be specifically described by way of the examples below, but the present invention is not limited thereto.

In the following examples and comparative examples, the concentration of sugars, oligosaccharide purity, turbidity, filterability of oligosaccharide liquid, concentration of proteins, β-glucosidase (BGL) activity, preparation of cellulase derived from *Trichoderma*, concentration of ethanol, and fermentation of ethanol and lactic acid using a soybean oligosaccharide liquid were measured as follows.

Reference Example 1: Measurement of Sugar Concentration

The concentration of each of the monosaccharides (glucose, galactose, fructose, sucrose, raffinose, and stachyose) contained in the sugar liquid (aqueous solution) obtained in each of Examples and Comparative Examples was analyzed under high performance liquid chromatography (HPLC) conditions described below and quantified by comparison with a standard sample.
(HPLC Conditions)
Instrument: ACQUITY UPLC system (manufactured by Waters)
Column: ACQUITY UPLC BEH Amide 1.7 μm 2.1×100 mm Column (manufactured by Waters)
Mobile phase: Liquid A; 80% acetonitrile+0.2% TEA, Liquid B; 30% acetonitrile+0.2% TEA
Flow rate: 0.12 mL/min
Temperature: 35° C.

Reference Example 2: Measurement of Oligosaccharide Purity

A value obtained by, based on the following equation (1), dividing the total value of the mass (g) of each oligosaccharide (sucrose, raffinose, stachyose) measured by the method described in the above Reference Example 1 by the mass (g) of the total solids (TS) in the aqueous solution was used as oligosaccharide purity (%). The mass of the total solids in the aqueous solution was measured using an infrared moisture determination balance (FD-720, manufactured by Kett).

Oligosaccharide purity (%)=Total value (g) of mass of each oligosaccharide (sucrose, raffinose, stachyose)/mass (g) of TS in aqueous solution   (1)

Reference Example 3: Measurement of Turbidity

The turbidity of aqueous solution was measured using a turbidimeter (portable turbidimeter, 2100P, manufactured by Hach) (unit: NTU). It is to be noted that the upper limit of the turbidity measurement by this device is 1000 NTU and therefore the turbidity above the measurement upper limit in the following Examples and Comparative Examples is all indicated as "not less than 1000 (NTU)".

Reference Example 4: Evaluation of Filterability of Oligosaccharide Liquid

In order to evaluate whether a membrane filtration process was applicable or not for each soybean oligosaccharide liquid used in the following Examples and Comparative Examples, an ME filtration rate (mL/min) was measured. The measurement was carried out by subjecting 100 mL of oligosaccharide liquid to suction filtration using a microfiltration membrane (hydrophilic Durapore, manufactured by Millipore) with a fine pore size of 0.45 μm and a diameter of 47 mm at 25° C. and −50 kPa(G). At that time, time (min.) required for the filtration was measured. A value obtained by dividing liquid volume (100 mL) by this value was used as the MF filtration rate. It is to be noted that in cases where the time required for the filtration of 100 mL of oligosaccharide liquid was above 30 minutes, that is, the filtration rate was below 3.3 mL/min., the liquid was considered not to be suitable for practical use and regarded as "impossible to be filtered".

It is to be noted that, as a reference, when pure water was subjected to filtration using the above method, the MF filtration rate of pure water was 390 mL/min.

Reference Example 5: Measurement of Protein Concentration

The concentration of proteins in an aqueous solution was measured using a measurement kit according to Bradford method (Quick Start Bradford Protein Assay, manufactured by Bio-Rad).

Reference Example 6: Measurement of β-Glucosidase (BGL) Activity and BGL Specific Activity Measurement of the BGL activity of an aqueous solution was carried out in accordance with a method for "Cellobiase assay" described in "Pure & Appl. Chem., Vol. 59, No. 2, pages 257-268". The reaction conditions were 50° C. and pH 5.0; the BGL activity was calculated as an activity per 1 mL of enzyme liquid (unit: U/mL). Further, based on the concentration of proteins measured by the method described in the above Reference Example 5, the BGL activity per mg of protein was calculated (this is hereinafter referred to as "BGL specific activity", unit: U/mg). It is to be noted that 1 unit (U) of BGL activity is defined as an enzymatic activity that breaks down 1 μmol of cellobiose in a cellobiose breakdown reaction for one minute (or generates 2 μmol of glucose for one minute).

Reference Example 7: Preparation of Cellulase Derived from *Trichoderma*

Cellulase derived from *Trichoderma* was prepared by the following method.
(Preculture)
To distilled water, corn steep liquor 5% (w/vol), glucose 2% (w/vol), ammonium tartrate 0.37% (w/vol), ammonium sulfate 0.14 (w/vol), potassium dihydrogen phosphate 0.2% (w/vol), calcium chloride dihydrate 0.03% (w/vol), magnesium sulfate heptahydrate 0.03% (w/vol), zinc chloride 0.02% (w/vol), iron chloride (III) hexahydrate 0.01% (w/vol), copper sulfate (II) pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol) were added such that each indicated concentration was attained. Thereafter, 100 mL of the distilled water containing each of the above components was placed in a 500 mL-erlenmeyer flask with baffles followed by autoclave sterilization at 121° C. for 15 minutes. After the resultant was allowed to be cooled, PE-M and Tween 80, each of which had been separately subjected to autoclave sterilization at 121° C. for 15 minutes, were each added to the above 500 mL-erlenmeyer flask with baffles at 0.01% (w/vol). To this preculture medium, *Trichoderma reesei* PC3-7 was inoculated so as to be $1 \times 10^5$ microbial cells/mL and cultured at 28° C. with shaking at 180 rpm for 72 hours using a shaking device (BIO-SHAKER BR-40LF manufactured by TAITEC Corporation), and the resultant culture was used as a preculture.

(Main Culture)

To distilled water, corn steep liquor 5% (w/vol), glucose 2% (w/vol), cellulose (Avicel) 10% (w/vol), ammonium tartrate 0.37% (w/vol), ammonium sulfate 0.14% (w/vol), potassium dihydrogen phosphate 0.2% (w/vol), calcium chloride dihydrate 0.03% (w/vol), magnesium sulfate heptahydrate 0.03% (w/vol), zinc chloride 0.02% (w/vol), iron chloride (III) hexahydrate 0.01% (w/vol), copper sulfate (II) pentahydrate 0.004% (w/vol), manganese chloride tetrahydrate 0.0008% (w/vol), boric acid 0.0006% (w/vol), and hexaammonium heptamolybdate tetrahydrate 0.0026% (w/vol) were added such that each indicated concentration was attained. Thereafter, 2.5 L of the distilled water containing each of the above components was placed in a 5 L-stirring jar (DPC-2A manufactured by ABLE Corporation) vessel followed by autoclave sterilization at 121° C. for 15 minutes. After the resultant was allowed to be cooled, PE-M and Tween 80, each of which had been separately subjected to autoclave sterilization at 121° C. for 15 minutes, were each added to the above 500 mL-erlenmeyer flask with baffles at 0.1% (w/vol) and 250 mL of *Trichoderma reesei* PC3-7 that had been in advance precultured in the liquid medium by the above-mentioned method was inoculated. The above *Trichoderma reesei* was then cultured at 28° C. with shaking at 300 rpm for 87 hours using a shaking device (BIO-SHAKER BR-40LF manufactured by TAITEC Corporation) with an aeration volume of 1 vvm. Thereafter, the resulting culture was centrifuged at 3000 G for 10 minutes and then the supernatant was subjected to membrane filtration (STERICUP-GV, material: PVDF, manufactured by Millipore). This culture solution prepared in the above-mentioned condition was used in the examples below as cellulase derived from *Trichoderma*.

Reference Example 8: Measurement of Ethanol Concentration

The concentration of ethanol in an aqueous solution was detected and calculated by a flame ionization detector under gas chromatography (GC) conditions shown below and quantified by comparison with a standard sample.
Instrument: Shimadzu GC-2010 (manufactured by Shimadzu Corporation)
Column: TC-1 (inner diameter 0.53 mm, length 15 m, membrane thickness 1.50 μm(manufactured by GL Sciences Inc.)
Detection method: flame ionization detector (FID)

Reference Example 9: Measurement of Lactic Acid Concentration

The concentration of lactic acid in an aqueous solution was quantified under HPLC conditions shown below by comparison with a standard sample.

Column: Shim-Pack SPR-H (manufactured by Shimadzu Corporation)
Mobile phase: 5 mM β-toluenesulfonic acid (flow rate 0.8 mL/min)
Reaction solution: 5 mM β-toluenesulfonic acid, 20 mM bis tris, 0.1 mM EDTA.2Na (flow rate 0.8 mL/min)
Detection method: electrical conductivity
Temperature: 45° C.

Reference Example 10: Fermentation Production of Ethanol and Lactic Acid Using Soybean Oligosaccharide Liquid (Preculture)

In a test tube, 2 ml of YPD medium described below was placed and subjected to autoclave sterilization at 121° C. for 20 minutes. After the resulting culture was allowed to cool, one of the yeast colonies formed by plate culture (30° C., 24 hours) in YPD agar medium described below was inoculated using a platinum loop in a clean bench. This was cultured at 30° C. with shaking at 120 rpm for 24 hours using a shaking device (BIO-SHAKER BR-40LF manufactured by TAITEC Corporation), thereby obtaining a preculture liquid.
YPD medium: yeast extract 1% (w/vol), Bactopeptone (manufactured Difco) 2% (w/vol), glucose 2% (w/vol)
YPD agar medium: containing agar 2% (w/vol) in addition to the above YPD medium composition (Main Culture 1: Fermentation Production of Ethanol)

An aqueous potassium hydroxide solution (5 mol/L) was added to a soybean oligosaccharide liquid which served as a fermentation raw material so that the pH was adjusted to 5.5. From this, 10 mL was placed in a test tube together with 0.5 mL of the above preculture liquid and mixed. This test tube was cultured at 30° C. with shaking at 120 rpm for 43 hours.

(Main Culture 2: Fermentation Production of Lactic Acid)

An aqueous potassium hydroxide solution (5 mol/L) was added to a soybean oligosaccharide liquid which served as a fermentation raw material so that the pH was adjusted to 5.5; calcium carbonate was further added thereto so as to attain a final concentration of 2% (w/vol). From this, 10 mL was placed in a test tube together with 0.5 mL of the above preculture liquid and mixed. This test tube was cultured at 30° C. with shaking at 120 rpm for 68 hours.

Example 1: Production of Purified Soybean Oligosaccharide Liquid (Step (1): Recovery of Soybean Oligosaccharide by Means of Polar Organic Solvent)

After commercially-available pure soy milk and 96% (vol/vol) ethanol were mixed at a liquid volume ratio of 3:7, the liquid mix was fully stirred. This was centrifuged at 8000 G for 1 minute using a centrifugation device; after centrifugation, an oligosaccharide liquid that contains a polar organic solvent was recovered as the supernatant.

(Step (2): Evaporation Removal of Polar Organic Solvent)

Of the supernatant obtained in the above step (1), 600 mL was placed in a 1 L-recovery flask and concentrated under reduced pressure at 50° C. and 230 hPa using a rotary evaporator (NVC-2100, manufactured by Tokyo Rikakikai Co., Ltd./EYELA) and a hot water bath (SB-1000, manufactured by Tokyo Rikakikai Co., Ltd./EYELA). After the concentration was carried out until the liquid volume became 150 mL, the remaining liquid was recovered as a soybean oligosaccharide suspension. It is to be noted that this step was repeated until a required amount of soybean oligosaccharide suspension was obtained. The sugar concentration, oligosaccharide purity, turbidity, and total solid concentration (TS concentration) in the obtained soybean oligosaccharide suspension were measured by the method described in Reference Examples 1 to 3. The results are shown in Table 1.

TABLE 1

|  |  | Soybean oligosaccharide suspension |
|---|---|---|
| Sugar concentration (g/L) | Glucose | 0 |
|  | Galactose | 0 |
|  | Fructose | 7.2 |
|  | Sucrose | 129.4 |
|  | Raffinose | 14.1 |
|  | Stachyose | 79.1 |
| Oligosaccharide purity |  | 50 wt % |
| Turbidity |  | Not less than 1000 NTU |
| Total solid concentration (TS concentration) |  | 45 wt % |

(Step (3): Treatment of Soybean Oligosaccharide Suspension with Cellulase)

The soybean oligosaccharide suspension obtained in the above step (2) was diluted in water so that the total solid concentration was adjusted to about 35%. The pH was adjusted to about pH 5.0 using sulfuric acid (3 mol/L) and the resultant was stirred well. Thereafter, about 1 mL of commercially-available cellulase preparation (Accellerase DUET (hereinafter, referred to also as DUET), manufactured by Genencor) was added to 1 L of liquid volume and mixed; the mixture was stirred at about 50° C. for 24 hours, thereby obtaining a cellulase-treated soybean oligosaccharide suspension.

(Step (4): Recovery of Purified Soybean Oligosaccharide Liquid)

The pH of the cellulase-treated soybean oligosaccharide suspension obtained in the above step (3) was adjusted to about pH 2.5 using sulfuric acid (3 mol/L) and stirred; thereafter the resultant was aliquoted into a centrifuge tube and left to stand in the centrifuge tube. One hour later, the centrifuge tube was directly set to a centrifugation device; centrifugation was carried out at 8000 G for one minute. After the centrifugation, a purified soybean oligosaccharide liquid was recovered as the supernatant. The oligosaccharide purity, turbidity, and MF filtration rate of the recovered purified soybean oligosaccharide liquid were measured according to Reference Examples 2 to 4. The results are shown in Table 2.

Comparative Example 1: Cases where the Step (3) (Cellulase Treatment) was not Carried Out The same treatment as described in Example 1 was carried out except that the cellulase treatment in the step (3) of Example 1 was omitted. That is, instead of the cellulase-treated solution, the soybean oligosaccharide suspension obtained in the step (2) was used in the step (4) of Example 1 (note that the suspension was diluted in water so that the total solid concentration thereof was about 35%). As a result, even after the soybean oligosaccharide suspension was centrifuged in the step (4), hardly any precipitation was generated and any suspended matters were unable to be separated. The oligosaccharide purity, turbidity, and MF filtration rate of this soybean oligosaccharide suspension in which the suspended matter remained were measured according to Reference Examples 2 to 4. The results are shown in Table 2.

Comparative Example 2: Cases where Alcohol was not Added and Mixed

The same treatment as described in Example 1 was carried out except that the steps (1) and (2) were omitted. That is, instead of using the soybean oligosaccharide suspension, pure soy milk was directly used in the step (3) of Example 1. As a result, even after the centrifugation in the step (4), hardly any precipitations were generated and any suspended matters were unable to be separated. The oligosaccharide purity, turbidity, and MF filtration rate of this soy milk in which the suspended matter remained were measured according to Reference Examples 2 to 4. The results are shown in Table 2.

TABLE 2

|  | Step* | | | | Oligosaccharide purity (%) | Turbidity (NTU) | MF filtration rate (mL/min) |
|---|---|---|---|---|---|---|---|
|  | 1 | 2 | 3 | 4 |  |  |  |
| Example 1 | + | + | + | + | 84 | 6 | 218 |
| Comparative Example 1 | + | + | − | + | 51 | Not less than 1000 | Impossible to be filtered |
| Comparative Example 2 | − | − | + | + | 38 | Not less than 1000 | Impossible to be filtered |

As is clear from Table 2, in Comparative Example 2 in which the steps (1) and (2) were not carried out and the steps (3) and (4) were carried out, the oligosaccharide purity was low; the turbidity was above the upper limit of measurement; MF filtration was impossible. In Comparative Example 1 in which the steps (1), (2), and (4) were carried out and the step (3) was not, the oligosaccharide purity was higher than that in Comparative Example 2. However, the turbidity was above the upper limit of measurement and MF filtration was impossible as well. On the other hand, in Example 1 in which all of the steps (1) to (4) were carried out, the oligosaccharide purity was much higher than that in Comparative Example 2; the turbidity was, in addition, reduced markedly; MF filtration was possible as well. Thus, by carrying out the method for producing a purified soybean oligosaccharide liquid according to the present invention, a soybean oligosaccharide liquid that has high purity and high clarity is easy to be subjected to membrane filtration was able to be obtained.

Example 2: Cases where Various Cellulase Preparations were Used

As cellulase preparations containing various components, DUET used in Example 1, Novo 188 (manufactured by Sigma Aldrich), Trichoderma culture medium (described in Reference Example 7) were used. First, their protein concentration and BGL activity per protein were each measured according to Reference Examples 5 and 6. The results are shown in Table 3.

TABLE 3

| | Protein (g/L) | BGL specific activity (U/mg) |
|---|---|---|
| DUET | 38.5 | 14.0 |
| Novo 188 | 27.0 | 5.2 |
| Trichoderma culture medium | 24.2 | 1.1 |

The same treatment as described in Example 1 was each carried out except that these preparations were used as cellulase preparations and the added amount thereof was 1.4 mL for Novo 188 and 1.6 mL for Trichoderma culture medium so that the added amount was equal to that in Example 1 in terms of proteins. The oligosaccharide purity, turbidity, and MF filtration rate of each of the recovered purified soybean oligosaccharide liquids were measured according to Reference Examples 2 to 4. The results are shown in Table 4.

TABLE 4

| Example 2 | Oligosaccharide purity (%) | Turbidity (NTU) | MF filtration rate (mL/min) |
|---|---|---|---|
| Novo 188 | 84 | 10 | 177 |
| Trichoderma culture medium | 83 | 12 | 148 |

As is clear from Table 2 to Table 4, there was not much difference in the oligosaccharide purity and turbidity among the cases where any cellulase preparations were used. On the other hand, in cases where the cellulase preparation with higher BGL specific activity was used, the MF filtration rate was higher. Thus, it is preferred to use one with a higher BGL specific activity as the cellulase used in the method for producing a purified soybean oligosaccharide liquid according to the present invention.

Example 3: Cases where β-Glucosidase (Purified Product) was Used

As a cellulase preparation that only contains β-glucosidase, β-glucosidase derived from *Aspergillus niger* (E-BG-LUC, manufactured by Megazyme) was used. First, the protein concentration and BGL activity thereof were each measured according to Reference Examples 5 and 6. The results are shown in Table 5.

TABLE 5

| | Protein (g/L) | BGL specific activity (U/mg) |
|---|---|---|
| β-glucosidase | 2.1 | 127.6 |

The same treatment as described in Example 1 was carried out except that the amount of cellulase preparation having the BGL specific activity shown in Table 5 added was 2.0 mL so that the BGL activity was equal to that in Example 1 (absolute value) (about 540 Units, calculated based on a BGL specific activity value in Table 3) and this was used as cellulase. The oligosaccharide purity, turbidity, and MF filtration rate of the recovered purified soybean oligosaccharide liquid were measured according to Reference Examples 2 to 4. The results are shown in Table 6.

TABLE 6

| Example 3 | Oligosaccharide purity (%) | Turbidity (NTU) | MF filtration rate (mL/min) |
|---|---|---|---|
| β-glucosidase | 84 | 9 | 138 |

As is clear from Table 2, Table 4, and Table 6, almost compatible results of the oligosaccharide purity and turbidity were obtained even from the cellulase preparation that only contains β-glucosidase (Example 3), as compared to other cellulase preparations. Also, as for the MF filtration rate, a sufficient rate was obtained. Thus, in the step (3) of the method for producing a purified soybean oligosaccharide liquid according to the present invention, it is presumed that β-glucosidase in the cellulase mainly promotes aggregation precipitation of suspended substances, thereby contributing to improve MF filterability. Further, although the BGL activity added was the same, the MF filtration rate of Example 3 was lower, as compared with that of Example 1. It is thus presumed that an effect of improving the MF filterability is concertedly enhanced by other cellulase components. Therefore, it is thought that one containing various enzyme components is more preferred as the cellulase used in the method for producing a purified soybean oligosaccharide liquid according to the present invention.

Comparative Example 3: Cases where Enzyme Preparations Other than Cellulase were Used As an enzyme preparation other than cellulase, protease (derived from *Aspergillus oryzae*, manufactured by Sigma-Aldrich) was used. First, the protein concentration thereof were measured according to Reference Example 5, as a result, was found to be 1100 g/L. The same treatment as described in Example 1 was each carried out except that this protease was used instead of DUET as an enzyme preparation and in addition the added amount thereof was 35 μL so as to be the same in terms of proteins as that in Example 1.

As a result, even after the centrifugation in the step (4), hardly any precipitations were generated and any suspended matters were unable to be separated. The oligosaccharide purity, turbidity, and MF filtration rate in this soybean oligosaccharide liquid in which the suspended matter remained were measured according to Reference Examples 2 to 4. The results are shown in Table 7.

TABLE 7

| Comparative Example 3 | Oligosaccharide purity (%) | Turbidity (NTU) | MF filtration rate (mL/min) |
|---|---|---|---|
| Protease | 52 | Not less than 1000 | Impossible to be filtered |

As is clear from Table 7, when protease was used instead of cellulase, none of oligosaccharide purity, turbidity, and MF filtration rate were good.

Example 4: Cases where Cellulase and Esterase were Used Together

As esterase, lipase 1 (lipase AS Amano, manufactured by Wako Pure Chemical Industries, Ltd.) and lipase 2 (Lipase, from *Aspergillus niger*, manufactured by Sigma-Aldrich) were used. First, 0.1 g of powder of each esterase was dissolved in 0.5 mL of 50 mmol/L sodium acetate buffer (pH 5.2). As a result of the measurement of their protein concentrations according to Reference Example 5, the protein concentrations of lipases 1 and 2 was 9.3 g/L and 8.7 g/L, respectively. The same treatment as described in Example 1 was each carried out except that these esterases were further added in addition to DUET. It is to be noted that the amount of lipase 1 added was 410 μL and the amount of lipase 2 added was 440 μL so that the amount of lipase 1 and lipase 2 added was each equal to ¹/₁₀ of the amount of proteins of DUET added. The oligosaccharide purity, turbidity, and MF filtration rate of the recovered purified soybean oligosaccharide liquid were measured according to Reference Examples 2 to 4. The results are shown in Table 8.

TABLE 8

| Example 4 | Oligosaccharide purity (%) | Turbidity (NTU) | MF filtration rate (mL/min) |
|---|---|---|---|
| DUET + lipase 1 | 84 | 2 | 264 |
| DUET + lipase 2 | 84 | 4 | 248 |

As is clear from Table 2 and Table 8, when esterase was further added in addition to cellulase, the turbidity was able to be further reduced and the MF filtration rate further improved, as compared with the case of using cellulase alone.

Example 5: Study on pH Effects

The same treatment as described in Example 1 was each carried out except that the pH of the cellulase-treated soybean oligosaccharide suspension in the step (4) was 6.0, 5.0, 4.0, 3.5, 3.1, 3.0, 2.5, or 2.0 (it is to be noted that the case of pH 2.5 was the same condition as described in Example 1 and thus the results of Example 1 were actually used). It is to be noted that pH adjustment was carried out by adding 1 mol/L sodium hydroxide or 3 mol/L sulfuric acid. The oligosaccharide purity, turbidity, and MF filtration rate of the recovered purified soybean oligosaccharide liquid were measured according to Reference Examples 2 to 4. The results are shown in Table 9.

TABLE 9

| Example 5 pH | Oligosaccharide purity (%) | Turbidity (NTU) | MF filtration rate (mL/min) |
|---|---|---|---|
| 6.0 | 83 | 43 | 106 |
| 5.0 | 82 | 36 | 112 |
| 4.0 | 83 | 31 | 129 |
| 3.5 | 83 | 34 | 132 |
| 3.1 | 83 | 26 | 150 |
| 3.0 | 84 | 13 | 200 |
| 2.5 | 84 | 6 | 218 |
| 2.0 | 84 | 7 | 220 |

As is clear from Table 2 and Table 9, regardless of the pH, the oligosaccharide purity was equal to that of Example 1. On the other hand, it was found that, as compared with that in Comparative Examples 1 and 2, the turbidity was greatly reduced at any pH of the cellulase-treated soybean oligosaccharide suspension, and further reduced in the case in which the pH was not more than 3.0. Similarly, it was found that, as compared with that in Comparative Examples 1 to 3, the MF filtration rate greatly improved at any pH, and further improved in the case in which the pH was not more than 3.0.

Example 6: Addition of Alkaline Earth Metal Salt

The same treatment as described in Example 1 was carried out except that 10 g of calcium carbonate or calcium chloride was added instead of using sulfuric acid to carry out the pH adjustment in the step (4). The oligosaccharide purity, turbidity, and MF filtration rate of the recovered purified soybean oligosaccharide liquid were measured according to Reference Examples 2 to 4. The results are shown in Table 10.

TABLE 10

| Example 6 | Oligosaccharide purity (%) | Turbidity (NTU) | MF filtration rate (mL/min) |
|---|---|---|---|
| Addition of calcium carbonate | 80 | 9 | 205 |
| Addition of calcium chloride | 79 | 6 | 190 |

As is clear from Table 10, the same oligosaccharide purity, turbidity, and MF filtration rate as those in Example 1 were attained even in the case in which either of calcium carbonate or calcium chloride was added.

Example 7: Effects of Total Solid Concentration and Enzyme Amount

For cases where, in the step (3), the total solid concentration after addition of water was set to four kinds, i.e., 45% (w/w), 40% (w/w), 35% (w/w), and 30% (w/w), and further the amount of cellulase preparation (DUET) added was, for each kind, set to three kinds, i.e., 0.1 mL, 1 mL, and 10 mL, that is, for 12 cases in total, the same treatment as described in Example 1 was each carried out except for the total solid concentration and the amount of cellulase (it is to be noted that the conditions employed when the total solid concentration was 35% (w/w) and the amount of cellulase added was 1 mL were the same as those described in Example 1 and thus the results of Example 1 were actually used).

The oligosaccharide purity, turbidity, and MF filtration rate of the recovered purified soybean oligosaccharide liquid were measured according to Reference Examples 2 to 4. The results are shown in Table 11.

TABLE 11

| Total solid concentration (% (w/w)) | Amount of enzyme added (mL) | Oligo-saccharide purity (%) | Turbidity (NTU) | MF filtration rate (mL/min) |
|---|---|---|---|---|
| 45 | 0.1 | 54 | Not less than 1000 | Impossible to be filtered |
|  | 1 | 54 | Not less than 1000 | Impossible to be filtered |
|  | 10 | 81 | 12 | 108 |
| 40 | 0.1 | 50 | Not less than 1000 | Impossible to be filtered |
|  | 1 | 80 | 58 | 119 |
|  | 10 | 82 | 9 | 225 |
| 35 | 0.1 | 83 | 10 | 209 |
|  | 1 | 84 | 6 | 218 |
|  | 10 | 84 | 3 | 230 |
| 30 | 0.1 | 81 | 7 | 231 |
|  | 1 | 84 | 4 | 240 |
|  | 10 | 82 | 7 | 247 |

As is clear from Table 11, when the total solid concentration was not more than 35%, there was not much difference in the oligosaccharide purity, turbidity, and MF filtration rate in any of the cases where the amount of cellulase used was 0.1 mL, 1 mL, and 10 mL. On the other hand, in the case in which the total solid concentration was above 40% (w/w), 0.1 mL was not enough for the amount of cellulase used. From this, in order to attain the same results as described in Example 1, it was found that the amount of cellulase used is required to be 10 mL. Therefore, it can be said that if the method for producing a purified soybean oligosaccharide liquid according to the present invention is used, the amount of enzyme used is able to be greatly reduced by adjusting the total solid concentration of soybean oligosaccharide suspension to not more than 35%.

Figure 1:
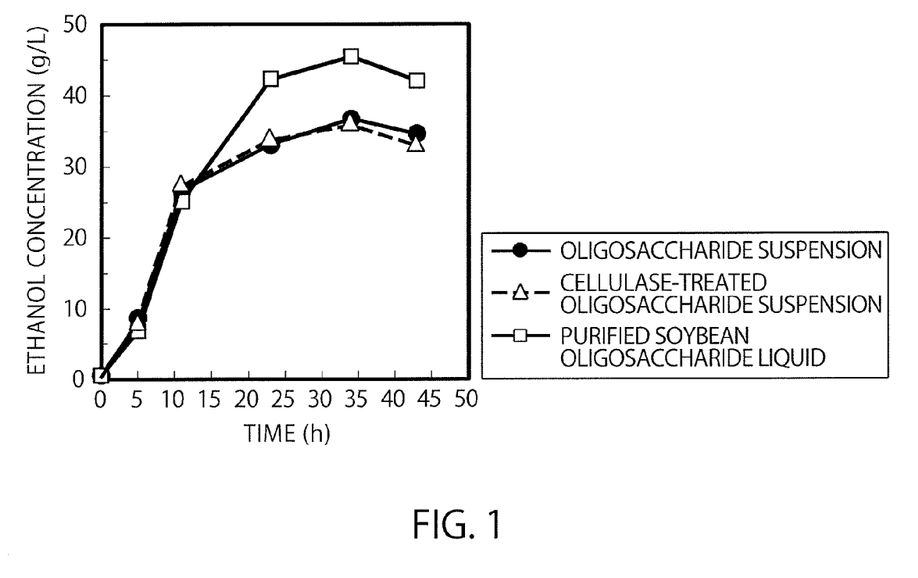
FIG. 1 shows a change in the concentration of ethanol with time.
Figure 2:
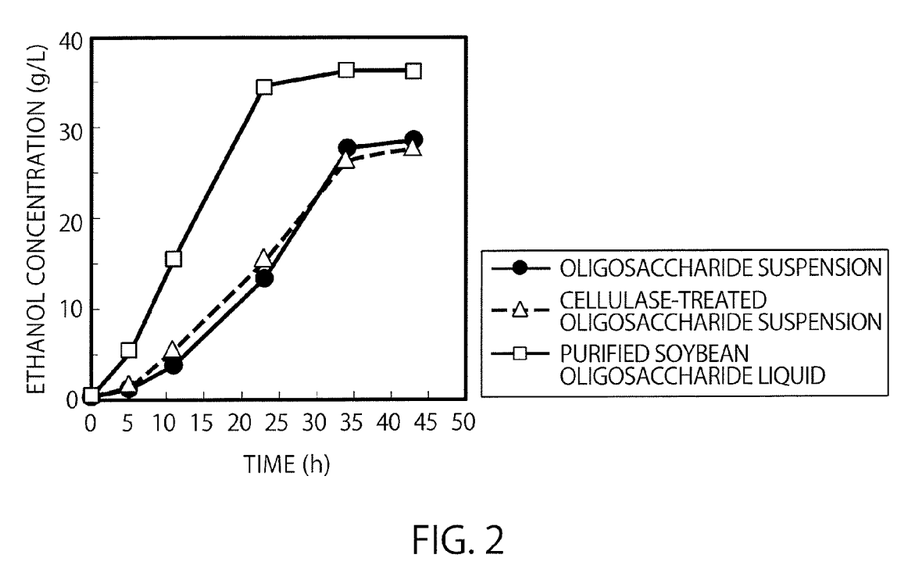
FIG. 2 shows a change in the concentration of ethanol with time.
Figure 3:
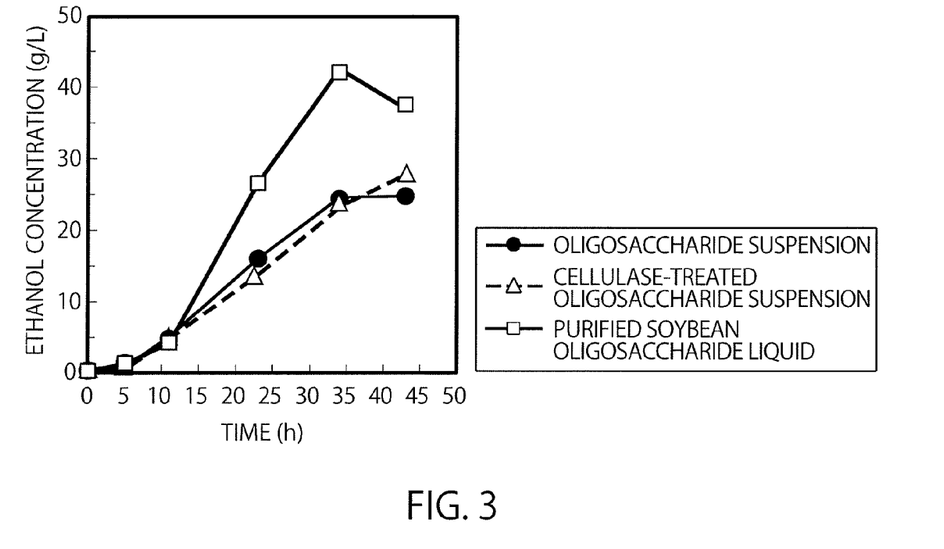
FIG. 3 shows a change in the concentration of ethanol with time.

Example 8: Fermentation Production of Ethanol Using Soybean Oligosaccharide Liquid For cases where, in the fermentation production method for ethanol described in Reference Example 8, three kinds of yeast, i.e., *Saccharomyces cerevisiae* OC2 strain (ATCC 46276), *Candida tropicalis* NBRC0199 strain, and *Candida utilis* NBRC0988 strain were used and three kinds of raw materials, i.e., the soybean oligosaccharide suspension obtained in the step (2), the cellulase-treated soybean oligosaccharide suspension obtained in the step (3), and the purified soybean oligosaccharide liquid obtained in the step (4), as described in Example 1, were used for each yeast, that is, for nine cases in total, the fermentation production of ethanol was carried out. A change in the concentration of ethanol in each reaction solution with time is shown in FIG. 1 to FIG. 3. It is to be noted that: FIG. 1 shows the case of using *Saccharomyces cerevisiae* OC2 strain (ATCC 46276) as yeast; FIG. 2 shows the case of using *Candida tropicalis* NBRC0199 strain as yeast; and FIG. 3 shows the case of using *Candida utilis* NBRC0988 strain as yeast.

As is clear from FIG. 1 to FIG. 3, in the case where any yeast was used, both production rate and final accumulation concentration of ethanol increased only when the purified soybean oligosaccharide liquid was used as a raw material.

Figure 4:
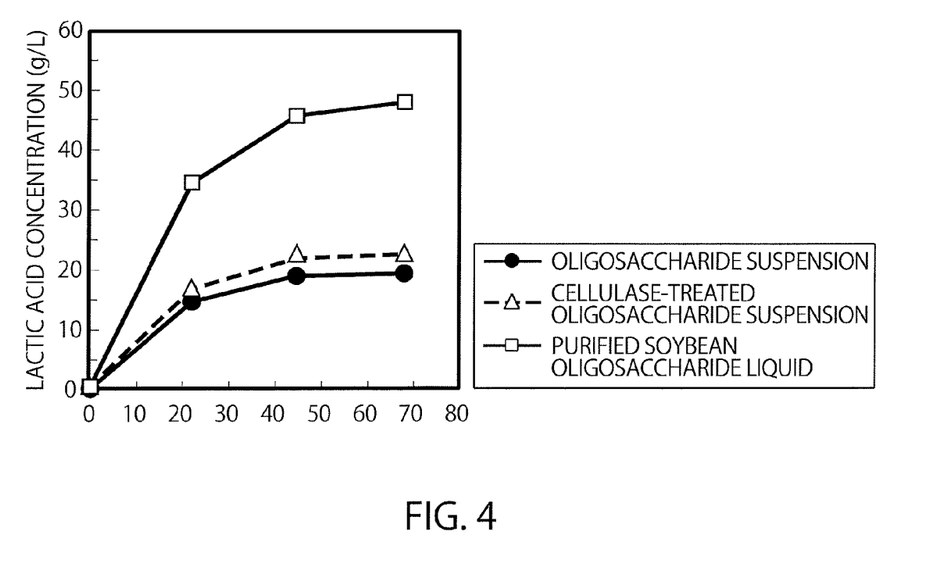
FIG. 4 shows a change in the concentration of lactic acid with time.

Example 9: Fermentation Production of Lactic Acid Using Soybean Oligosaccharide Liquid For cases where, in the fermentation production method for lactic acid described in Reference Example 8, D-lactic acid-producing yeast prepared by a method described in WO 2010/140602 was used as yeast and three kinds of soybean oligosaccharide liquids, i.e., the soybean oligosaccharide suspension obtained in the step (2), the cellulase-treated soybean oligosaccharide suspension obtained in the step (3), and the purified soybean oligosaccharide liquid obtained in the step (4), as described in Example 1, were each used for the yeast, that is, for three cases in total, the fermentation production of lactic acid was carried out. A change in the concentration of lactic acid in each reaction solution with time is shown in FIG. 4. As is clear from FIG. 4, both production rate and final accumulation concentration of lactic acid increased only when the purified soybean oligosaccharide liquid was used as a raw material.

The invention claimed is:

1. A method for producing a purified soybean oligosaccharide liquid from a soybean and/or a processed soybean product, the method comprising:

the step (1) of mixing the soybean and/or the processed soybean product with a water-containing polar organic solvent that contains a polar organic solvent and water and then removing a generated precipitate to obtain a soybean oligosaccharide liquid that contains the water-containing polar organic solvent;

the step (2) of removing the polar organic solvent from the soybean oligosaccharide liquid to obtain a soybean oligosaccharide suspension;

the step (3) of mixing the soybean oligosaccharide suspension with cellulase to obtain a cellulase-treated soybean oligosaccharide suspension; and the step (4) of subjecting the cellulase-treated soybean oligosaccharide suspension to solid-liquid separation to obtain a purified soybean oligosaccharide liquid.

2. The method for producing a purified soybean oligosaccharide liquid according to claim 1, wherein the cellulase comprises one type or two or more types selected from the group consisting of: β-glucosidase, cellobiohydrolase, and endoglucanase.

3. The method for producing a purified soybean oligosaccharide liquid according to claim 1, wherein the soybean oligosaccharide liquid is subjected to heating and/or pressure reduction to remove the polar organic solvent in the step (2).

4. The method for producing a purified soybean oligosaccharide liquid according to claim 1, wherein the total solid concentration in the soybean oligosaccharide suspension is adjusted in a range of 10 to 35% (w/w) before mixing with the cellulase in the step (3).

5. The method for producing a purified soybean oligosaccharide liquid according to claim 1 that comprises the step (5) of further purifying the purified soybean oligosaccharide liquid using one type or two or more types of separation membranes selected from the group consisting of: a microfiltration membrane, an ultrafiltration membrane, a nanofiltration membrane, and a reverse osmosis membrane.

6. The method for producing a purified soybean oligosaccharide liquid according to claim 1, wherein the pH of the cellulase-treated soybean oligosaccharide suspension is adjusted in a range of 1.0 to 6.0 in the step (4).

7. The method for producing a purified soybean oligosaccharide liquid according to claim 1, wherein an alkaline earth metal salt is mixed into the cellulase-treated soybean oligosaccharide suspension in the step (4).

8. The method for producing a purified soybean oligosaccharide liquid according to claim 1, further comprising mixing an esterase into the soybean oligosaccharide suspension in the step (3).

9. The method for producing a purified soybean oligosaccharide liquid according to claim 1, wherein ethanol is used as the polar organic solvent.

10. The method for producing a purified soybean oligosaccharide liquid according to claim 1, wherein when the soybean and/or the processed soybean product are/is mixed with the water-containing polar organic solvent in the step (1), the concentration of the polar organic solvent that is calculated by the following equation (1) is in a range of 50 to 90% (w/w)

$$\text{Concentration of polar organic solvent} = \text{Mass of polar organic solvent in water-containing polar organic solvent}/(\text{Mass of water contained in soybean and/or processed soybean product} + \text{Total mass of water-containing polar organic solvent}) \qquad (I).$$

* * * * *